United States Patent [19]
Fischell

[11] Patent Number: 6,146,323
[45] Date of Patent: Nov. 14, 2000

[54] DELIVERY CATHETER FOR A RADIOISOTOPE STENT

[75] Inventor: Robert E. Fischell, Dayton, Md.

[73] Assignee: IsoStent, Inc., Belmont, Calif.

[21] Appl. No.: 09/311,876

[22] Filed: May 14, 1999

[51] Int. Cl.[7] .................................................. A61N 5/00
[52] U.S. Cl. ................................................................ 600/3
[58] Field of Search ............................................. 600/1–8

[56] References Cited

U.S. PATENT DOCUMENTS

| | | | |
|---|---|---|---|
| 5,059,166 | 10/1991 | Fischell et al. | 600/3 |
| 5,302,168 | 4/1994 | Hess | 600/3 |
| 5,411,466 | 5/1995 | Hess | 600/3 |
| 5,484,384 | 1/1996 | Ferrot | 600/3 |
| 5,730,698 | 3/1998 | Fischell et al. | 600/3 |
| 5,879,282 | 3/1999 | Fischell et al. | 600/3 |

*Primary Examiner*—Max Hindenburg

[57] ABSTRACT

Disclosed is a stent delivery catheter system for placing a radioactive stent within a blockage in a vessel of a human body. The stent delivery catheter system consists of a radioactive stent that is placed onto an angioplasty balloon that is located at the distal portion of a stent delivery catheter. Just proximal and just distal to the stent there is a proximal radioactive band and a distal radioactive band, respectively, each of which are generally thin walled and cylindrical. The radioactive stent located on the balloon at the distal portion of the stent delivery catheter is advanced over a flexible guide wire until the non-deployed radioactive stent is placed at the site of a vessel blockage such as an arterial stenosis. The balloon is inflated and the radioactive stent and the distal and proximal radioactive bands are pushed radially outward in apposition to the wall of the artery, resulting in dilatation of the stenosis. The balloon remains expanded for several minutes, which maintains the proximal radioactive band and the distal radioactive band against the artery wall at positions that are just proximal and just distal to the edges of the stent. By this means, the regions of the vessel wall that are just proximal and just distal to the edges of the stent experience a sufficient dose of radiation so that the cells in that region become incapable of producing growth factor.

11 Claims, 2 Drawing Sheets

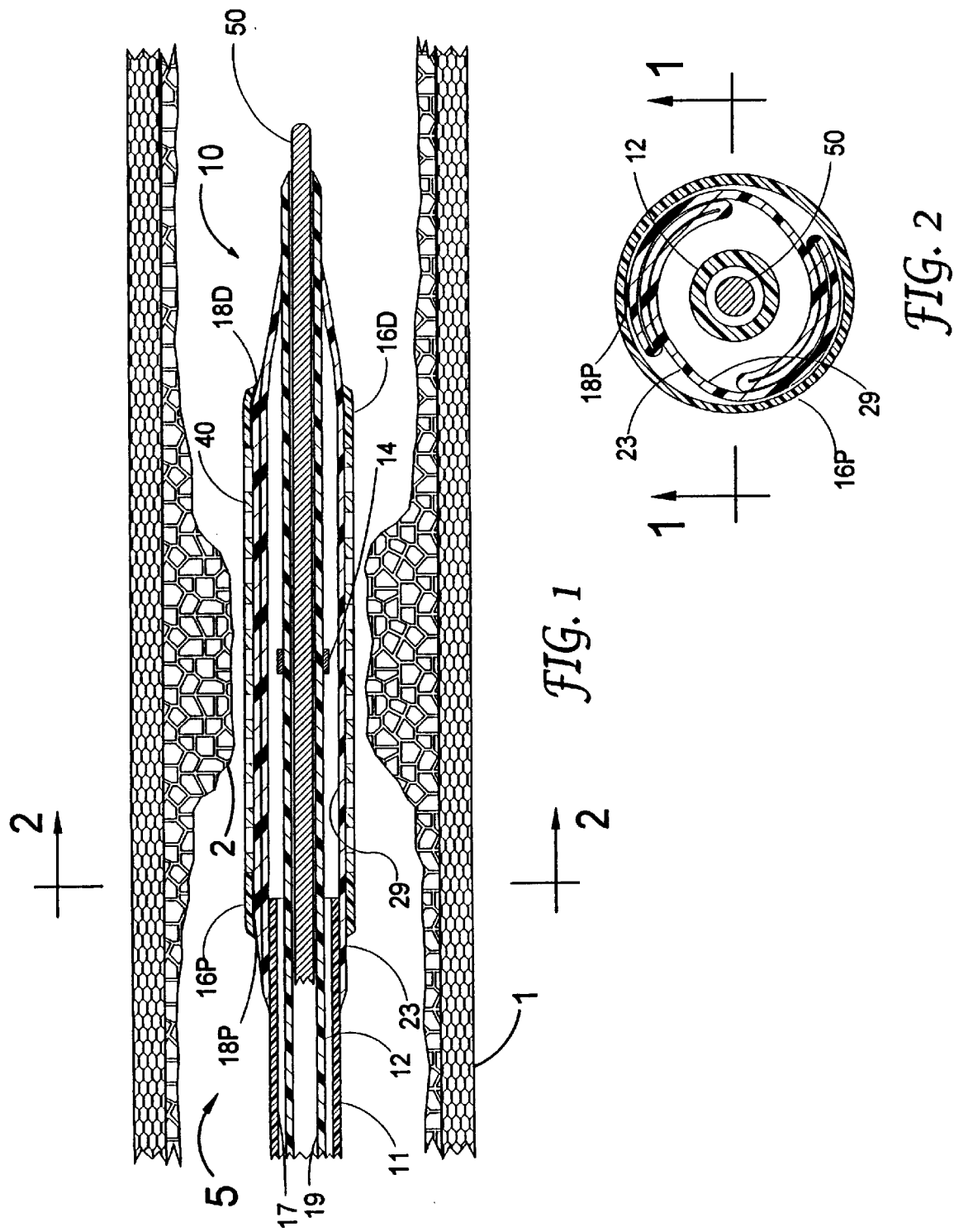

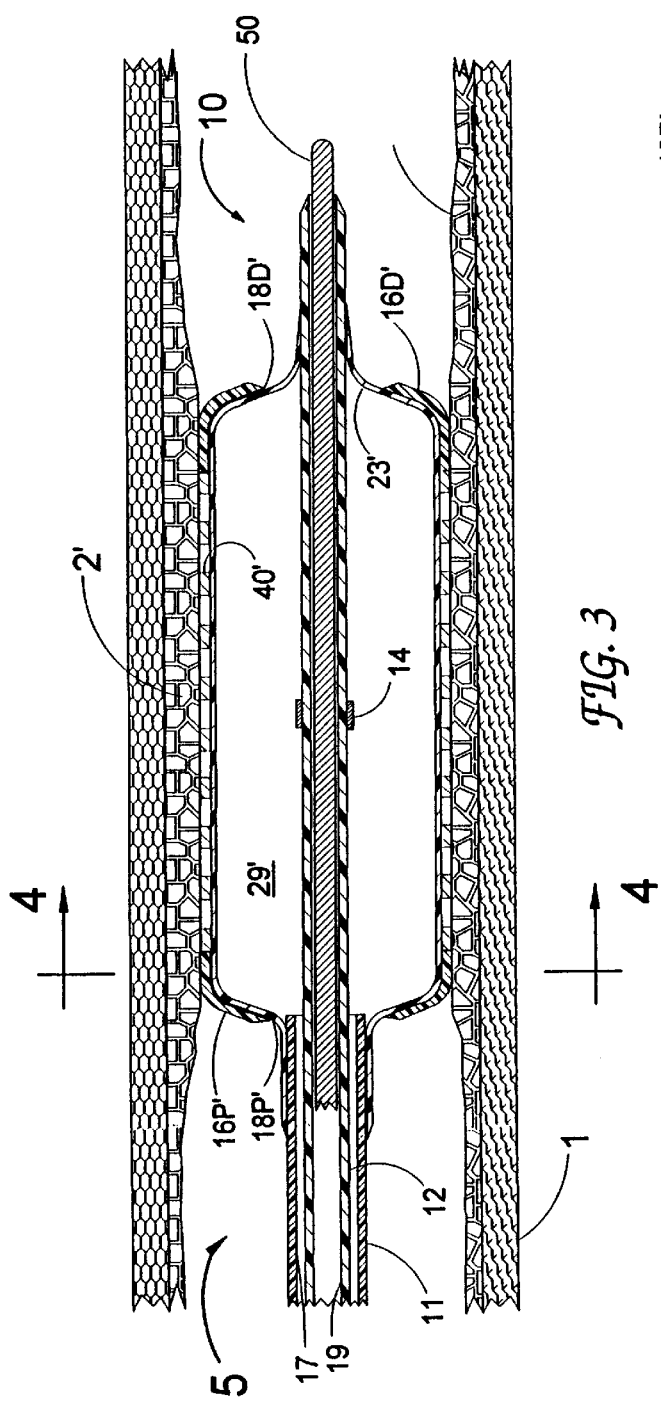
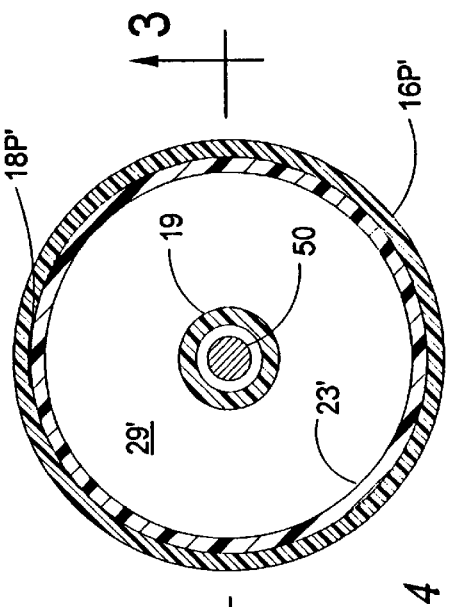

DELIVERY CATHETER FOR A RADIOISOTOPE STENT

FIELD OF USE

This invention is in the field of devices to treat vascular obstructions.

BACKGROUND OF THE INVENTION

In U.S. Pat. No. 5,059,166 by Fischell et al is described a radioisotope stent for the treatment of arterial stenoses. In clinical trials, this radioactive stent has been shown to decrease neointimal hyperplasia within the stent but in some patients an "edge effect" has been observed. The edge effect is characterized by a short length of stenosis that appears just proximal or just distal to the edge of the stent. When the edge effect is severe, the blood flow in that artery can be severely diminished.

In U.S. Pat. No. 5,879,282, Fischell et al describe a variety of balloon angioplasty catheter systems each having an inflatable balloon that includes an elastic radioactive section for catheter based radiation of an arterial stenosis. However, this Fischell patent does not consider using such an expandable radioactive source for delivering a radioactive stent to eliminate a vascular blockage such as an arterial stenosis. Moreover, in U.S. Pat. No. 5,879,282, Fischell et al do not consider using an expandable radioactive source to reduce the edge effect that occurs with the use of a radioactive stent.

SUMMARY OF THE PRESENT INVENTION

The present invention is a stent delivery catheter system for placing a radioactive stent within a blockage in a vessel of a human body. The stent delivery catheter system consists of a radioactive stent that is placed onto an angioplasty balloon located at the distal portion of a stent delivery catheter. Just proximal and just distal to the stent there is a proximal radioactive band and a distal radioactive band, respectively, each of which are generally thin walled and cylindrical.

The radioactive stent that is located on the balloon at the distal portion of the stent delivery catheter is advanced over a flexible guide wire until the non-deployed radioactive stent is placed at the site of a vessel blockage such as an arterial stenosis. The balloon is inflated and the radioactive stent and the distal and proximal radioactive bands are pushed radially outward in apposition to the wall of the artery, resulting in dilatation of the stenosis. The balloon remains expanded for several minutes, which maintains the proximal radioactive band and the distal radioactive band against the artery wall at positions that are just proximal and just distal to the edges of the stent. By this means, the regions of the vessel wall that are just proximal and just distal to the edges of the stent experience a sufficient dose of radiation so that the cells in that region become incapable of producing growth factor. In addition, by this means, the edge effect that can be encountered with a radioisotope stent is avoided.

After the edge regions of the vessel wall have been sufficiently irradiated, the balloon is deflated and the stent delivery catheter with the proximal and distal radioactive bands and the guide wire are all removed from the patient's vascular system.

Another embodiment of this invention utilizes a radiopaque marker band located under the balloon and centered between the proximal end and the distal end of the radioactive stent.

Another embodiment of this invention utilizes proximal and distal radioactive bands that are radiopaque.

Another embodiment of this invention utilizes a perfusion guide wire that perfuses oxygen distally to the stent delivery catheter.

Thus it is an object of this invention to use a single stent delivery system to both place a radioactive stent at the site of a vascular obstruction and to irradiate the regions of the vessel wall that are just proximal and just distal to the edges of the radioactive stent.

Another object of this invention is to provide a means for irradiating a vessel wall just proximal and just distal to a radioactive stent by placing generally cylindrical radioactive bands in close proximity to that vessel wall just proximal and just distal to the stent.

These and other important objects and advantages of this invention will become apparent from the detailed description of the invention and the associated drawings provided herein.

BRIEF DESCRIPTION OF THE DRAWINGS

FIG. 1 is longitudinal cross section of the distal section of a stent delivery catheter system as it would be placed into an arterial stenosis prior to stent deployment, the stent delivery catheter system having an angioplasty balloon with a mounted stent and cylindrical radioactive bands placed just proximal and just distal to the stent.

FIG. 2 is a highly enlarged transverse cross section of the stent delivery catheter system at section 2—2 of FIG. 1.

FIG. 3 shows a longitudinal cross section of the distal section of a stent delivery catheter system with the balloon inflated, the radioactive stent deployed outward so as to dilate the stenosis and the radioactive bands in apposition to the artery wall.

FIG. 4 is a highly enlarged transverse cross section of the stent delivery catheter system at section 4—4 of FIG. 4.

DETAILED DESCRIPTION OF THE INVENTION

FIG. 1 is a longitudinal cross section of the distal portion of the stent delivery catheter system 5. The stent delivery catheter system 5 consists of a balloon stent delivery catheter 10, a radioactive stent 40 and a guide wire 50. The distal portion of the stent delivery catheter system 5 is already advanced over the guide wire 50 until the non-deployed radioactive stent 40 is centered within an arterial stenosis 2 located within an artery 1.

The distal section of the balloon catheter 10 consists of an outer shaft 11, an inner shaft 12, a proximal radioactive band 16P, and a distal radioactive band 16D. An annular passageway 17 lies between the inner surface of the outer shaft 11 and the outer surface of the inner shaft 12. A central lumen 19 allows the passage of the guide wire 50. At the distal section of the stent delivery catheter system 5, the balloon catheter 10 has a distal portion which includes an angioplasty balloon 23 whose interior chamber 29 is in fluid communication with the annular passageway 17. Thus, a source of inflation fluid can be inserted into or removed through the annular passageway 17 and the chamber 29 to inflate and deflate the balloon 23. Mounted on the balloon 23 is a radioactive balloon expandable stent 40 of any design that is well known in the art of radioactive balloon expandable stents. Also at the distal section of the balloon catheter 10 is a radiopaque marker band 14 located co-axially around the inner shaft 12 and under the angioplasty balloon 23. The radiopaque marker band 14 would be fixedly attached to the inner shaft 12 and centrally located between the proximal and distal ends of the radioactive stent 40.

The radiopaque marker band 14 is used to position the radioactive stent 40 within the stenosis 2.

The proximal radioactive band 16P is situated co-axially over the proximal section of the angioplasty balloon 23 and the distal radioactive band 16D is situated co-axially over the distal section of the angioplasty balloon 23. The bands 16P and 16D would be made from an elastic or plastic material into which a radioisotope such as the beta particle emitter phosphorous-32 or yttrium-90 could be impregnated making them radioactive. Although a beta particle emitting radioisotope is desirable, there are several gamma emitters having a comparatively short range in human tissue that could also be employed. An x-ray emitting radioisotope can also be used. In any case, a level of radioactivity of between 1 and 100 milliCuries would be suitable for each of the marker bands 16P and 16D. The proximal radioactive band 16P can be adhesively joined to the proximal section of the angioplasty balloon 23 along one narrow longitudinal line 18P as shown in FIGS. 1 and 2. Similarly, the distal radioactive band 16D can be attached to the distal section of the angioplasty balloon 23 along one narrow longitudinal line 18D. These types of attachments are required so that the balloon 23 can expand by unfolding without tearing or otherwise adversely distorting the cylindrical radioactive bands 16P and 16D.

It should be understood that the bands 16P and 16D could be formed from an elastic material such as silicone rubber or they could be formed from a comparatively non-elastic elastomer such as polyurethane. If formed from a plastic such as polyurethane, the bands 16P and 16D would be folded in a manner similar to the balloon 23.

FIG. 2 shows the enlarged transverse cross section of the stent delivery catheter system 5 at the section 2—2 of FIG. 1. It should be noted that between the radioactive band 16P and the angioplasty balloon 23 is the narrow attachment 18P, which extends in a longitudinal direction.

FIG. 3 shows the balloon 23' inflated by an inflation fluid injected in the proximal section of the annular passageway 17 and into the interior chamber 29' of the balloon 23' which causes the radioactive stent 40' to dilate the arterial stenosis 2'. It should be noted that the radioactive bands 16P' and 16D' and the narrow long attachment lines 18P' and 18D' become distorted when the balloon 23' is inflated and that the radioactive bands 16P' and 16D' are in apposition with the arterial stenosis 2' and the arterial wall 1. It should also be noted that during expansion of the balloon 23' the distal end of the proximal radioactive band 16P' remains in proximity to the proximal end of the radioactive stent 40' and the proximal end of the distal radioactive band 16D' remains in proximity to the distal end of the radioactive stent 40'.

The balloon 23' remains expanded for several minutes, which maintains the proximal radioactive band 16P' and the distal radioactive band 16D' against the stenosis 2' and the artery wall 1 at positions that are just proximal and just distal, respectively, to the edges of the radioactive stent 40'. If perfusion capability is not provided, the balloon 23' may have to be deflated for some period of time and then re-inflated to obtain additional radiation dosing of the arterial wall 1 in the regions just proximal and just distal to the edges of the radioactive stent 40'. By this means, the regions of the vessel wall 1 that are just proximal and just distal to the edges of the stent 40' experience a sufficient dose of radiation so that the cells in that region become incapable of producing growth factor. In addition, by this means, the edge effect that can be encountered with a radioisotope stent such as 40' is avoided.

After the balloon 23' is deflated, the radioactive bands 16P' and 16D' revert to their original shape as shown for the radioactive bands 16P and 16D in FIG. 1. Although the radioactive bands 16P' and 16D' shown in FIG. 3 are shown extending longitudinally over a portion of the balloon 23', it should be understood that the bands 16P' and 16D' could be shorter or longer. In particular, the proximal radioactive band 16P' can extend over the whole of the proximal section of the balloon 23' such that the proximal end of 16P' is in proximity to the proximal end of the balloon 23' and the distal radioactive band 16D' can extend over the whole of the distal section of the balloon 23' such that the distal end of 16D' is in proximity to the distal end of the balloon 23'.

FIG. 4 shows the enlarged transverse cross section of the stent delivery catheter system 5 at the section 4—4 of FIG. 3. It should be noted that the angioplasty balloon 23' is unfolded and expanded thereby expanding the radioactive band 16P'. It should also be noted that, when expanded, the angioplasty balloon 23' also expands the radioactive band 16D' as shown in FIG. 3.

Although the stent delivery catheter system 5 is most valuable for stenting of stenoses in coronary arteries, it should be understood that it could be used in any vessel of the human body. It should also be noted that the radioactive bands 16P and 16D exactly center the radioactive stent 40 on the balloon 23. Still further it should be noted that this invention can be used with either balloon expandable or self-expanding radioisotope stents, and the stent delivery catheter can be of either the "over-the-wire" design or of a "rapid-exchange" design.

It should also be noted that the bands 16P and 16D could be radiopaque as well as radioactive. The bands 16P and 16D would be molded from a highly elastic elastomer such as silicone rubber into which a powder from a high-density metal is placed. Such a metal could be tungsten, tantalum or any other highly radiopaque metal. Furthermore, a radioisotope such as the beta particle emitter phosphorous-32 or yttrium-90 could be impregnated into the marker bands 16P and 16D making them both radiopaque and radioactive. The radiopacity is used to indicate the position of the stent 40 on the delivery catheter 10 and the radioactivity is used to irradiate the arterial wall in the region just proximal and just distal to the edges of the stent 40. A radioisotope that is a gamma emitter could also be employed. If the bands 16P and 16D were both radioactive and radiopaque, the radiopaque marker band 14 could be eliminated. Since the radioisotope stent, especially prior to deployment, is clearly visible by fluoroscopy, the marker bands 16P and 16D must include a radioisotope but they need not necessarily be radiopaque; i.e., they need not necessarily include a high density metal.

It should be further understood that a method for continuously perfusing tissue distal to the balloon during the irradiation procedure could be used. A hollow guide wire that allows oxygenated fluid to pass through it could be used. J. R. Spears describes the use of such a hollow guide wire in U.S. Pat. No. 5,407,426.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A stent delivery catheter system for placing a radioactive stent within a stenosis of a vessel in a human body, the system comprising:

a flexible guide wire;

a stent delivery catheter; the stent delivery catheter having a distal portion; the stent delivery catheter having an angioplasty balloon adapted for inflation by injectable inflation fluid, the balloon being located at the distal portion of the stent delivery catheter and having a proximal and a distal end; the stent delivery catheter having a radioactive stent mounted co-axially around the angioplasty balloon; the radioactive stent having a proximal end and a distal end; the stent delivery catheter also having a proximal radioactive band and a distal radioactive band; the proximal and distal radioactive bands being generally thin walled and cylindrical; the proximal radioactive band having a distal end located in proximity to the proximal end of the radioactive stent; the distal radioactive band having a proximal end located in proximity to the distal end of the radioactive stent; the proximal and distal radioactive bands adapted to be moved in apposition to the vessel wall.

2. The system of claim 1 wherein the proximal and distal radioactive bands include a beta particle emitting radioisotope.

3. The system of claim 2 wherein the beta particle emitting isotope is phosphorous-32.

4. The system of claim 2 wherein the beta particle emitting isotope is yttrium-90.

5. The system of claim 1 wherein the proximal and distal radioactive bands include a gamma ray emitting radioisotope.

6. The system of claim 1 wherein the proximal and distal radioactive bands include an x-ray emitting radioisotope.

7. The system of claim 1 wherein the proximal and distal radioactive bands each have a radioactive activity level that lies between 1 and 100 milliCuries.

8. The system of claim 1 wherein the balloon angioplasty catheter has an inner shaft for the passage of the flexible guide wire; and located in the distal portion of the balloon angioplasty catheter a radiopaque marker band is located co-axially over the inner shaft and co-axially under the radioactive stent and is centered between the proximal and distal ends of the radioactive stent.

9. The system of claim 1 wherein the proximal and distal radioactive bands are radiopaque.

10. The system of claim 1 wherein the proximal radioactive band is adhesively joined to the proximal section of the angioplasty balloon along a narrow longitudinal line and the distal radioactive band is adhesively joined to the distal section of the angioplasty balloon along a narrow longitudinal line.

11. The system of claim 1 wherein the stent delivery catheter includes a guide wire lumen and an oxygenation guide wire is placed through the guide wire lumen to perfuse the tissue located distally to the angioplasty balloon.

* * * * *